United States Patent [19]

Nojiri et al.

[11] Patent Number: 5,026,838
[45] Date of Patent: Jun. 25, 1991

[54] PHOSPHORAMIDITE COMPOUNDS AND PROCESS FOR PRODUCTION THEREOF

[75] Inventors: Ryuji Nojiri, Aichi; Yoshihiro Hayakawa, Ichinomiya; Mamoru Uchiyama, Kawasaki; Hisatoyo Kato, Ohbu; Yasuyoshi Chino, Tokyo; Shinichiro Tahara, Yokohama, all of Japan

[73] Assignee: Nippon Zeon Co., Ltd., Tokyo, Japan

[21] Appl. No.: 229,773

[22] Filed: Aug. 4, 1988

Related U.S. Application Data

[63] Continuation of Ser. No. 909,728, Sep. 22, 1986, abandoned.

[30] Foreign Application Priority Data

Sep. 25, 1985 [JP] Japan ................. 60-211240
Oct. 7, 1985 [JP] Japan ................. 60-223138

[51] Int. Cl.$^5$ ................. C07H 19/167; C07H 19/173
[52] U.S. Cl. ......................... 536/27; 536/28; 536/29
[58] Field of Search ......................... 536/24, 26, 27-29

[56] References Cited

U.S. PATENT DOCUMENTS

| | | | |
|---|---|---|---|
| 3,847,898 | 11/1974 | Kelly et al. | 536/23 |
| 4,415,732 | 11/1983 | Caruthers et al. | 536/27 |
| 4,469,863 | 9/1984 | Ts'O et al. | 536/27 |
| 4,515,781 | 5/1985 | Torrence et al. | 536/27 |
| 4,661,777 | 5/1989 | Caruthers et al. | 536/27 |
| 4,725,677 | 2/1988 | Koster et al. | 536/27 |

FOREIGN PATENT DOCUMENTS 0090789 5/1983 European Pat. Off. .

OTHER PUBLICATIONS

Hayakawa, et al., *Journal of Organic Chemistry*, vol. 51, No. 12, "Allyloxycarbonyl Group: A Versatile Blocking Group for Nucleotide Synthesis", pp. 2400-2402, 1986.
Marugg, et al., *Tetrahedron Letters*, vol. 27, No. 20, "A New and Versatile Approach to the Preparation of Valuable Deoxynucleoside 3'-phosphite Intermediates", pp. 2271-2274, 1986.
Corey, et al., *Journal of Organic Chemistry*, vol. 38, No. 18, "Cleavage of Allyloxycarbonyl Protecting Group from Oxygen and Nitrogen Under Mild Conditions by Nickel Carbonyl", pp. 3223-3224, 1973.
Guibe, et al., *Tetrahedron Letters*, vol. 22, No. 37, "The Allyloxy-carbonyl Group for Alcohol Protection: Quantitative Removal or Transformation into Allyl Protecting Group Via Pi-allyl Complexes of Palladium", pp. 3591-3594, 1981.
Kunz, et al., Agnew. Chem. Int. Ed. Engl, vol. 23, No. 6, "The Allyl-Carbonyl (Aloc) Moiety-conversion of an Unsuitable Into a Valuable Amino Protecting Group for Peptide Synthesis", pp. 436-437, 1984.
Ikehara et al., "The Synthesis of Polynucleotides", pp. 135-213 in Advances in Carbohydrate Chemistry, vol. 36, 1979.

*Primary Examiner*—Johnnie R. Brown
*Assistant Examiner*—L. Eric Crane
*Attorney, Agent, or Firm*—Sherman & Shalloway

[57] ABSTRACT

Phosphoramidite compounds of the general formula

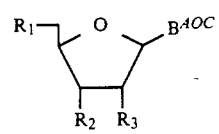

[I]

wherein each of $R_1$ and $R_2$ represents a hydroxyl group having a protective group, or the group $-OR_4$, $R_3$ represents a hydrogen atom, a hydroxyl group having a protective group, or the group $-OR_4$, $R_4$ represents the group

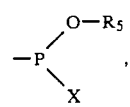

X represents a secondary amino group, $R_5$ represents an allylic residue or a protective group capable of being split off by beta-cleavage, and $B^{AOC}$ represents a nucleoside base residue in which the amino or imino group is protected with an allyloxycarbonyl-type residue, with the proviso that only one of $R_1$, $R_2$ and $R_3$ represents the group $-OR_4$. The compounds can be produced by reacting a nucleoside represented by the general formula

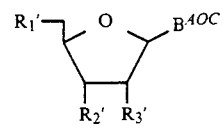

wherein each of $R_1'$ and $R_2'$ represents a hydroxyl group which may have a protective group, $R_3'$ represents a hydrogen atom, or a hydroxyl group which may have a protective group, and $B^{AOC}$ is as defined, with the proviso that only one of $R_1'$, $R_2'$ and $R_3'$ is a hydroxyl group, with a phosphoramide compound represented by the general formula

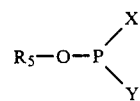

wherein X and $R_5$ are as defined, and Y represents a secondary amino group or a halogen atom.

14 Claims, No Drawings

PHOSPHORAMIDITE COMPOUNDS AND PROCESS FOR PRODUCTION THEREOF

This application is a continuation of Ser. No. 909,728 filed Sept. 22, 1986 now abandoned.

This invention relates to novel nucleoside phosphoramidite compounds, and a process for production thereof. More specifically, this invention relates to novel nucleoside phosphoramidite compounds having an allylic residue or a protective group capable of being split off by beta-cleavage and an allyloxycarbonyl-type residue respectively as protective groups for the hydroxyl group in the phosphoric acid moiety and the amino group in the base moiety, and to a process for production thereof.

Research work has been actively done on the chemical synthesis of polynucleotides such as DNA (deoxyribonucleic acid) and RNA (ribonucleic acid) which are important materials in gene technology recently showing a striking advance.

Previously, the diphosphate ester method, the triphosphate method and the phosphite method, for example, have been known for the chemical synthesis of polynucleotides. In any of these methods, the nucleotide monomer is subjected to condensation reaction after protecting the hydroxyl group in the phosphoric acid moiety and the amino group in the nucleoside base in order to avoid side reactions.

Recently, a method was developed in which a protective group capable of being split off by beta-cleavage, such as a beta-cyanoethyl group, a beta-halogenoethyl group or a beta-nitroethyl group, is used as a protective group for the hydroxyl group in place of the methyl group which has frequently been used in the prior art (see, for example, WO85/00816, and Tetrahedron Letters, vol. 24, No. 52, pages 5843-5846). Since the protective group capable of being split off by beta-cleavage can be more easily eliminated than the methyl group, this method makes it possible to circumvent the thiophenol treatment which is the disadvantage of the prior art. When applied to solid-phase synthesis, it has the advantage that the hydroxyl group in the phosphoric acid moiety can be deprotected at the same time as the removal of the carrier by treatment with ammonia. The method, however, has the disadvantage that a benzoyl group, an isobutyryl group, etc. are used as protective groups for the amino group, and in order to remove these protective groups, the product should be treated with hot aqueous ammonia for long periods of time.

It has now been found in accordance with this invention that by using an allylic residue or a protective group capable of being split off by beta-cleavage as a protective group for the hydroxyl group and an allyloxy-carbonyl-type residue as a protective group for the amino group, the protective groups can be eliminated rapidly under mild conditions, and that these protective groups are very stable during the polynucleotide synthesis reaction.

Thus, according to this invention, there is provided a phosphoramidite compound represented by the following general formula

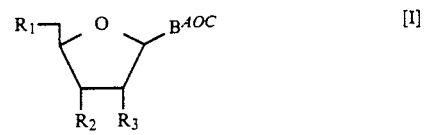

wherein each of $R_1$ and $R_2$ represents a hydroxyl group having a protective group, or the group $-OR_4$, $R_3$ represents a hydrogen atom, a hydroxyl group having a protective group, or the group $-OR_4$, $R_4$ represents the group

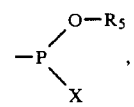

X represents a secondary amino group, $R_5$ represents an allylic residue or a protective group capable of being split off by beta-cleavage, and $B^{AOC}$ represents a nucleoside base residue in which the amino or imino group is protected with an allyloxycarbonyl-type residue, with the proviso that only one of $R_1$, $R_2$ and $R_3$ represents the group $-OR_4$.

According to another aspect of this invention, there is provided a process for producing the phosphoramidite compound of general formula [I] above, which comprises reactin9 a nucleoside represented by the general formula

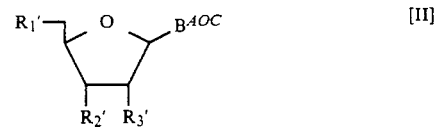

wherein each of $R_1'$ and $R_2'$ represents a hydroxyl group which may have a protective group, $R_3'$ represents a hydrogen atom, or a hydroxyl group which may have a protective group, and $B^{AOC}$ is as defined, with the proviso that only one of $R_1'$, $R_2'$ and $R_3'$ is a hydroxyl group,
with a phosphoramide compound represented by the general formula

wherein X and $R_5$ are as defined, and Y represents a secondary amino group or a halogen atom.

The nucleoside phosphoramidite compound of this invention is characterized in that the hydroxyl group in the phosphoric acid moiety is protected with an allylic residue or a protective group capable of being split off by beta-cleavage and the amino or imino group in the nucleoside base is protected with an allyloxycarbonyl-type residue.

In general formula [I], each of $R_1$ and $R_2$ represents a hydroxyl group having a protective group or the group $-OR_4$. The protective groups may be any of those which are generally used in nucleoside chemistry. Specific examples include trityl, monomethoxytrityl, dimethoxytrityl, trimethylsilyl, triethylsilyl, triphenylsilyl, t-butyldimethylsilyl, tetrahydropyranyl, 4-methoxyhydrofuranyl, benzoyl, benzyl, tetrahydrofuranyl, methoxymethyl, methoxyethoxymethyl, phenoxymethyl, methylthiomethyl and phenylthiomethyl groups.

$R_4$ is a residue of a phosphine represented by the formula

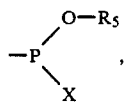

in which $R_5$ is (1) an allylic residue or (2) a group capable of being split off by beta-cleavage.

The allylic residue may be any of allylic groups which do not essentially impede the deprotecting reaction. Specific examples include allyl, methallyl, crotyl, prenyl, geranyl, cinnamyl and p-chlorocinnamyl groups. The number of carbon atoms of these protective groups is not particularly restricted, but is preferably not more than 10.

The protective group capable of being split off by beta-cleavage is represented by the following general formula

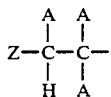

[IV]

wherein A represents a hydrogen atom or a lower alkyl group such as a methyl or ethyl group, and Z represents an electron attracting residue. Specific examples of the electron attracting residue Z are a cyano group, a nitro group, a thiocyano group, fluoro, chloro, bromo, a phenylsulfonyl group, a methylsulfonyl group, and a phenyl group. The phenyl group may have a substituent such as halogen atoms, cyano groups and a nitro group at its ortho-position and/or para-position. Of these, the protective groups in which Z is a cyano group, especially a beta-cyanoethyl group, are preferred.

Specific examples of the secondary amino group X include dimethylamino, diethylamino, diisopropylamino, di-t-butylamino, methylpropylamino, methylhexylamino, methylcyclohexylamino, ethylbenzylamino, morpholino, thiomorpholino, pyrrolidino, piperidino, 2,6-dimethylpiperidino, piperazino, imidazolino and pyrrolino groups. Those having not more than 10 carbon atoms are preferred.

Y represents the same secondary amino group as X, or a halogen atom such as chlorine, bromine or iodine. The secondary amino group is preferred.

$R_3$ represents a hydrogen atom, a hydroxyl group having a protective group, or the group $—OR_4$. The protective group and $R_4$ are the same as described above.

The nucleoside phosphoramidite of this invention is used as a monomer for synthesis of polynucleotides, and for this purpose, the group $—OR_4$ is introduced into only one of $R_1$, $R_2$ and $R_3$.

$B^{AOC}$ is a nucleoside base in which the amino or imino group is protected with an allyloxycarbonyl-type residue. Specific examples of nucleosides having a nucleoside base are deoxyadenosine, deoxyguanosine, deoxycytidine, adenosine, guanosine, cytidine and inosine.

The allyloxycarbonyl-type residue used as a protective group for the amino group of the base moiety may be any known protective group which does not essentially impair the deprotecting reaction. Specific examples include allyloxycarbonyl, methallyloxycarbonyl, crotyloxycarbonyl, prenyloxycarbonyl, cinnamyloxycarbonyl, p-chlorocinnamyloxycarbonyl and chloroallyloxycarbonyl groups.

The number of carbon atoms of the allyloxy-carbonyl-type residue may be properly selected by considering the separation of by-products formed by the reaction or the ease of obtaining the starting materials. Usually, this residue has not more than 12 carbon atoms.

Only one of $R_1'$, $R_2'$ and $R_3'$ is a hydroxyl group. If a hydroxyl group in $R_1'$, $R_2'$ or $R_3'$ has a protective group, the protective group may be the same as those described above.

The nucleoside used in this invention can be easily obtained by reacting a non-protected nucleoside with an allylating agent such as allyl chloroformate, allyl bromoformate or allyl (1-benzotriazoyl)carbonate in the presence of a base such as triethylamine or n-butyllithium in a solvent such as tetrahydrofuran or hexamethylphosphoric triamide.

The phosphoramide compound may, for example, be produced by the following method although it differs depending upon the type of $R_5$ For example, when $R_5$ is an allylic residue, the phosphoramide compound can be easily obtained by reacting a hydroxydihalogenophosphine such as hydroxydichlorophosphine with an allylating agent typified by allyl bromide to form an allyloxydihalogenophosphine, and reacting it with a secondary amine in a suitable solvent such as diethyl ether. When $R_5$ is a protective group capable of being split off by betacleavage, the phosphoramide compound can be easily obtained by reacting a phosphorus halide typified by phosphorus trichloride with an alcohol of the general formula $R_5—OH$, and then reacting the product with a secondary amine in a suitable solvent such as diethyl ether.

In both cases, the phosphoramide compound may also be obtained by reacting a phosphorus halide with a secondary amine to form a bisaminomonohalogenophosphine, and reacting it with an alcohol of the general formula $R_5—OH$.

The phosphoramidite compound of this invention may be produced in a customary manner except that the nucleoside and the phosphoramide compound represented by general formulae [II] and [III] are used as starting materials.

For example, the desired phosphoramidite compound can be efficiently obtained by reacting 1 mole of the nucleoside [II] and 1 to 3 moles of the phosphoramide compound [III] at 0 to 40° C. for 1 to 5 hours in the presence of a solvent.

The product may be isolated from the reaction mixture and purified by known means such as adsorptive chromatography, ion-exchange chromatography, partition by orgnanic solvents, and crystallization from organic solvents which are properly selected and combined.

The protective groups for the hydroxyl group of the phosphoric acid moiety and the amino or imino group of the nucleoside base in the resulting phosphoramidite compound of the invention may be rapidly eliminated under mild conditions. For example, by using the phosphoramidite compound in a given reaction, then oxidizing the phosphite moiety to a phosphate and thereafter treating the compound with a 0-valent palladium compound and a nucleophilic reagent typified by amines or formic acid salts under neutral conditions, the protective group in the nucleoside base moiety can be eliminated at room temperature within a short period of time.

Deprotection of the hydroxyl group differs depending upon the type of $R_5$ in general formula [I]. If $R_5$ is an allylic residue, it can be carried out in the same way as in the case of deprotecting the nucleoside base moiety. In this case, therefore, the nucleoside base moiety and the hydroxyl group moiety can be deprotected at the same time. If $R_5$ is a protective group capable of being split off by beta-cleavage, the deprotection can be easily carried out by treating the compound with aqueous ammonia at room temperature for 0.1 to 5 hours. In the case of solid-phase synthesis using a carrier, cutting from the carrier can be simultaneously effected during the above treatment.

The allylic residue, the protective group capable of being split off by beta-cleavage and the allyloxycarbonyl residue exist very stably under general conditions for a deprotecting reaction of the hydroxyl group of a saccharide portion (for example, deprotection of the 5'-hydroxyl group with trichloroacetic acid or deprotection of the 3'-hydroxyl group with tetra-n-butyl ammonium fluoride). The allylic residue exists very stably under the ammonia treating conditions frequently used for removal of the carrier.

The following examples illustrate the present invention more specifically.

REFERENTIAL EXAMPLE 1

Dimethylamine (156 millimoles) was dissolved in 80 ml of diethyl ether, and then 34.7 millimoles of allyloxydichlorophosphine was added. The mixture was stirred at room temperature for 12 hours. After the reaction, the resulting dimethylammonium chloride was filtered, and the ether solution was distilled to give allyloxybis(N,N-dimethylamino)phosphine as an oil in a yield of 76 mole%. The product showed the following properties.

(1) Boiling point: 93–94° C. (48 mmHg)
(2) $^1$H-NMR($C_6D_6$)
2.55(d, J=12.8Hz, 12H, 4NCH$_3$),
4.15(ddt, J=11.0, 4.8, 1.5Hz, 2H, C=CCH$_2$),
5.08(ddd, J =10.1, 2.0, 1.5Hz, 1H,
cis C$\underline{H}$=CHCH$_2$), 5.34(ddd, J=15.1, 2.0
1.5Hz, 1H, trans CH=CHCH$_2$),
5.90(ddt, J=15 1, 10.1, 4.8Hz, 1H,
CH$_2$=C$\underline{H}$CH$_2$).
(3) $^{31}$P NMR($C_6D_6$—$C_6H_6$ 1:4)
138.36

REFERENTIAL EXAMPLE 2

Referential Example 1 was repeated except that diisopropylamine was used instead of dimethylamine. Allyloxybis(N,N-diisopropylamino)phosphine was obtained in a yield of 55 mole%.

(1) Boiling point: 130–133 °C/6 mmHg
$^1$H NMR($C_6D_6$)
1.17(dd, J=7.8, 1.8Hz, 24H, 4NCH(CH$_3$)$_2$),
3.53(d.sept, J=10.8, 7.8Hz, 4H, 4NC$\underline{H}$),
4.10(ddt, J=10, 5, 2Hz, 2H, C=CCH$_2$),
5.07(m, 1H, cis CH=CHCH$_2$), 5.33 (m, 1H,
trans CH=CHC$\underline{H}$ ), 5.93 (ddt, J=18, 10, 5Hz,
1H, C$\underline{H}_2$=CHCH2).
($3^{31}$ P NMR($\overline{C}_6D_6$—$C_6H_6$, 1:4)
123.58

REFERENTIAL EXAMPLE 3

A 50 ml flask was charged with 4.77 millimoles of deoxyadenosine (compound 1) whose 5'-hydroxyl group and 3'-hydroxyl group were protected with a monomethoxytrityl group and a t-butyldimethylsilyl group, respectively. The inside of the flask was filled with an argon atmosphere, and the compound was dissolved in 50 ml of dry tetrahydrofuran. Then, t-butyllithium was added in an amount of 2 equivalents per equivalent of compound 1, and the mixture was stirred at −78° C. for 5 minutes. A solution of 1 equivalent, per equivalent of compound 1, of allyl(1-benzotriazoyl)carbonate in 50 ml tetrahydrofuran was added dropwise at room temperature over 25 minutes, and the reaction was carried out for 5 minutes. After the reaction, the solvent was evaporated, and the residue was dissolved in ethyl acetate and washed successively with water and a saturated aqueous solution of sodium chloride. The organic layer was then dried over magnesium sulfate, and the concentrated residue was chromatographed (silica 100 g, hexane/ethyl acetate=2/1) to give 5'-o-monomethoxytrityl-3'-o-t-butyldimethylsilyl-N-allyloxycarbonyldeoxyadenosine (compound 2) with the protection of the amino group of compound 1 with an allyloxycarbonyl group. The yield of the isolated compound 2 was 82%.

The compound 2 had the following properties.
(1) Analysis
Calculated: C=66.54, H=6.58, N=9.70;
Found: C=66.75, H=6.59, N=9.51.
(2) UV(CH$_3$OH)
216.6 nm$\lambda_{max}$), 234.0 nm (3) H$^1$—NMR(CDCl$_3$)
0.01, 0.04(each s. 6H 2Si<), 0.86 (s, 9H
Si+), 2.41(ddd, 1H(2'), J=4.2, 6.0, 13.2Hz),
2.79(ddd, 1H(2'), J=6.0, 6.0, 13.2Hz), 3.34
(dd, 2H(5'), J=3.0, 4.2Hz), 3.78 (s, 3H,
OCH$_3$), 4.0–4.13(m, 1H(4')) 4.45–4.65
(m, 1H(3')), 4.70 (d, 2H(allyl), J=5.7Hz),
5.13–5.45 (m, 2H

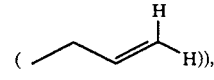

5.95 (tdd,

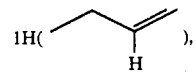

5.7, 10.2, 17.1Hz), 6.38 (dd,
1H(1'), J=6.0, 6.0Hz), 6.68(s, 1H(Ar)),
6.78(s, 1H(Ar)), 7.03–7.41(m, 12H(Ar)),
8.08(s, 1H), 8.63(s, 1H).

Then, 0.191 millimole of compound 2 was dissolved in 3 ml of tetrahydrofuran, and 0.96 millimole of tetra-n-butyl ammonium fluoride in the form of a solution in tetrahydrofuran was added dropwise. The mixture was then stirred for 20 minutes at room temperature. The solvent was evaporated, and the residue was worked up by the same operation as above except that 10 g of silica gel and a 15:1 mixture of chloroform and methanol were used in the chromatography. There was obtained 5'-mono-methoxytrityl-N-allyloxycarbonyl-2'-deoxyadenosine (compound 3) in a yield of 97%.

Compound 3 had the following properties.
(1) UV(CH₃CH)
267.2 nm $\lambda_{max}$), 233.2 nm
(2) ¹H NMR(CDCl₃)
2.42(d, 1H(OH), J=4.5Hz), 2.47(ddd, 1H(2'), J=4.5, 6.6, 13.2Hz), 2.87(ddd, 1H(2'), J=6.6, 6.6, 13.2Hz), 3.41(d, 2H(5'), J=4.8 Hz), 3.78(s, 3H, (OCH₃)), 4.15(dt, 1H(4'), J=4.2, 4.2Hz), 4.6–4.77(m, 1H(3')), 4.76 (tdd, 2H(allyl), J=1.8, 1.8, 5.7Hz), 5.17–5.52

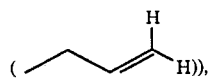

6.01 (tdd

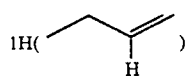

J=5.7, 9.6, 16.5Hz), 6.46 (dd,
1H(1'), 6.6Hz), 6.74(s, 1H(Ar)), 6.84(s, 1H(Ar)), 7.15-7.48(m, 12H(Ar)), 8.10(s, 1H), 8.47(s, 1H(amide)), 8.68(s, 1H).

REFERENTIAL EXAMPLE 4

1.5 Millimoles of 5'-o-monomethoxytritylthymidine and 1.56 millimoles of 1-H-tetrazole were dissolved in 12 ml of a 1:1 mixed solvent of tetrahydrofuran and acetonitrile, and 2.25 millimoles of allyloxybis(N,N-dimethylamino)phosphine was added at 0° C. The mixture was then stirred at 25° C. for 1.5 hours.

The reaction mixture was diluted with ethyl acetate which had been washed with a saturated aqueous solution of sodium bicarbonate. The diluted mixture was washed with a saturated aqueous solution of sodium chloride, and the organic layer was dried over magnesium sulfate and concentrated. The residue was dissolved in a 3:1 mixed solvent of toluene and hexane, and the solution was added to hexane with vigorous stirring at −78° C. to form a white precipitate. The precipitate was separated by filtration. Its yield was 71%. Analysis of the precipitate led to the determination that it was a phosphoramidite (compound 4) shown in Table 1 having the following properties.
(1) ¹H NMR(C₆D₆)
1.55(brs, 3H, C(5)CH ), 2.1-2.6(m, 8H, 2NCH₃, 2H₂'), 3.3-3.6(m, 5H, 2H₅'5, OCH₃), 4.1-4.4(m, 3H, H₄', 3.3-3.6 (m, 3H, CH₂=CCH₃'), 5.6–6.0(m, 1H, C=CHC), 6.53 (t-like, J=6Hz, 1H, H₁'), 6.7–6.9, 7.0–7.7 (m, 15, Aromatic H, C(5)H), 10.5(two s, 1H, N(3)H).
(2) IR(KBr)
3440, 3180, 1720, 1700, 1610, 1470, 1260 cm⁻¹.
(3) UV(CH₃CN)
$\lambda_{max}$ × 265.3 nm($\epsilon$=1.11×10⁴)
233.9 ($\epsilon$=1.56×10⁴)
(4) Analysis
Calculated for C₃₅N₄₀N₃O₇P:
C=65.10, H=6.26, N=6.50;
Found: C=65.42, H=6.20, N=6.45.

REFERENTIAL EXAMPLE 5

Three millimoles of 5'-o-monomethoxytritylthymidine and 3.1 millimoles of 1-H-tetrazole were dissolved in 20 milliliters of a 1:1 mixed solvent of tetrahydrofuran and acetonitrile, and then 4.5 millimoles of allyloxybis(N,N-diisopropylamino)phosphine was added at 0°. The mixture was stirred at 25° C. for 1.5 hours. Thereafter, the reaction mixture was mixed with an equal amount mixture of ethyl acetate and a saturated aqueous solution of sodium chloride. The organic layer was separated, washed with a saturated aqueous solution of sodium chloride, dried over magnesium sulfate and then concentrated. The residue was dissolved in toluene, and the solution was added to hexane with stirring at −78° C. to form a precipitate. The precipitate was separated by filtration. Its yield was 76%. Analysis of the precipitate led to the determination that it was a phosphoramidite (compound 5) shown in Table 1 having the following properties.
(1) ¹NMR(C₆D₆)
1.10(dd, J=8, 2Hz, 12H, 2NCH(CH₃)2, 1.57, 1.60(brs, 3H, C(5)CH ), 2.1–2.7(m, 2H, 2H₂'), 3.15(m, 2H, 2NCH), 3.4(m, 5H, 2H₅', OCH₃), 4.1(m, 1H, H₄'), 4.38(m, 2H, C=CCH₂), 5.03(m, 1H, cis CH=CHCH₂), .10(m, 1H, H₃'), 5.30(m, 1H, trans CH=CHCH₂), 5.77 (m,1H, C=CHCH₂), 6.50(t-like, J=6Hz, 1H, H₁'), 6.73–6.9, 7.0–7.7(m, 15H, Aromatic H, C(5)H), 10.4(brs, 1H, N(3)H).
(2) IR(KBr) 3420, 3180, 1720, 1690, 1600, 1450, 1250 cm⁻¹.
(3) UV(CH₃CN) $\lambda_{max}$=264.7 nm ($\Delta$=1.20×10⁴) 233.3 nm($\Delta$=1.64×10⁴)
(4) analysis
Calculated for C₃₉H₄₈N₃O₇P:
C=66.74, H=6.91, N=5.98;
Found: C=66, H=6.87, N=5.96.

EXAMPLE 1

0.2 Millimole of the 5'-o-monomethyoxytrityl-N-allyloxycarbonyl-2'-deoxyadenosine (coumpound 3) obtained in Referential Example 3 and 0.21 millimole of 1-H-tetrazole were dissolved in 2 ml of acetonitrile, and then 0.3 millimole of allyloxybis(morpholino)phosphine synthesized in accordance with Referential Example 1 was added. The mixture was stirred at 25° C. for 1.5 hours.

The reaction mixture was then diluted with 30 ml of ethyl acetate and then mixed with 15 ml of a 0.1 M potassium dihydrogen phosphate-sodium hydroxide buffer (pH 7.0). The organic layer was separated, washed with the same buffer, dried over magnesium sulfate and then concentrated. The residue ws chromatographed on a silica gel column (methanol:-chloroform=1:50) to give a phosphoramidite (compound 6) shown in Table 1 in a yield of 83%.
(1) ¹H NMR(CDCl₃)
2.5–3.2(m, 6H, 2H₂', 2 PNCH₂), 3.25-3.85 (m, 9H, 2H₅', 2 PNCCHO, OCH₃), 4.2–4.7 (m, 3H, allylic CH₂, H'), 4.74(d, 2H, J=6.7Hz, AO-C—CH2), 5.1–5.7(m, 5H, 2C=CH , H₃'), 5.85–6.2(m, 2H, 2 CCH=C), 6.47(dd, J=6, 7Hz, 1H 6.7–6.93, 7.15–7.55(m, 14H, aromatic H₁'), 8.07(s, 1H, H₂), 8.60(brs, 1H, NHCO), 8.64(s, 1H H₈).
(2) IR(CHCl₃) 3425, 3050, 1770, 1620, 1610, 1520, 1480, 1260 cm⁻¹
(3) UV(CH₃CN)
$\lambda_{max}$=266.5, 236.9, 223.5 nm
(4) Analysis
Calculated for C₄₁H₄₅N₆O₈P:
C=63.06, H=5.82, N=10.76;

Found: C=62.91, H=6.03, N=10.95.

EXAMPLE 2

1.5 Millimoles of 5'-o-monomethoxytrityl-N-allyloxycarbonyl-2'-deoxyguanosine and 1.56 millimoles of 1-H-tetrazole were dissolved in 12 ml of a 1:1 mixed solvent of tetrahydrofuran and acetonitrile, and then 2.25 millimoles of allyloxybis(N,N-dimethylamino)-phosphine was added at 0° C. The mixture was then stirred at 25° C. for 1.5 hours.

The reaction mixture was diluted with ethyl acetate which had been washed with a saturated aqueous solution of sodium bicarbonate. The diluted mixture was washed with a saturated aqueous solution of sodium chloride. The organic layer was dried over magnesium sulfate and concentrated. Then, the residue was dissolved in a 3:1 mixed solvent of toluene and hexane, and the solution was added to hexane with vigorous stirring at −78° C. to form a white precipitate. The precipitate was separated by filtration. Its yield was 71%. Analysis of the precipitate led to the determination that it was a phosphoramite (compound 7) shown in Table 1 having the following properties.

(1) 1H NMR($C_6D_6$)
2.1–2.6(m, 8H, 2 NCH , $2H_2$ '2), 3.3–3.7(m, 5H,
2 OCH ), 4.1–4.8(m, 5H, $H_4$'4, 2C=$CCH_2$),
5.6–6.0(m, 2H,
4.95–5.4(m, 5H, 2CH =C, H3
2C=CHC), 6.25(t-like, J=6Hz, $1H_1$'), 6.7–6.9,
7.0–7.7(m, 15, Aromatic H, C(8)H), 9.5–11.5(brs, 2H, N(1)H, NHCO).

(2) Analysis
Calculated for $C_{39}H_{43}N_6O_8P$:
C=62.06, H=5.74, N=11.13;
Found: C=62.28, H=5.81, N=11.10.

EXAMPLE 3

Three millimoles of 5'-o-monomethoxytrityl-N-allyloxycarbonyl-2'deoxycytidine prepared in accordance with Referential Example 3 and 3.1 millimoles of 1-H-tetrazole were dissolved in 20 ml of a 1:1 mixed solvent of tetrahydrofuran and acetonitrile, and then 4.5 millimoles of allyloxybis(N,N-diisopropylamino)phosphine was added at 0° C. The mixture was then stirred at 25° C. for 1.5 hours. The mixture was then mixed with an equal amount mixture of ethyl acetate and a saturated aqueous solution of sodium chloride. The organic layer was separated, washed with a saturated aqueous solution of sodium chloride, dried over magnesium sulfate, and concentrated. The residue was dissolved in toluene, and the solution was added to hexane with stirring at −78° C. to form a precipitate. The precipitate was separated by filtration. Its yield was 76%. Analysis of the precipitate led to the determination that it was a phosphoramidite (compound 8) shown in Table 1 having the following properties.

$^1$H NMR($C_6D_6$)
1.10(dd, J=8, 2Hz, 12H, 2 $NCH(CH_3)2$), 2.1–2.7
(m, 2H 2, 3.15(m, 2H, 2 NCH), 3.4(m,
5H, $2_5$', $OCH_3$), 4.1–4.8(m, 5H, $H_4$', 2=$CCH_2$),
4.95–5.4(m, 5H, $2CH_2$=C, $H_3$'),
5.77(m, 2H, 2C=CHCH ), 6.30(t-like, J=6Hz,
1H, $H_1$'), 6.73–6.9, 7.0–8.3(m, 16H,
aromatic H, C(5)H, C(6)H), 7.8(brs, 1H,
NHCO).
(2) Analysis
Calculated for $C_{42}H_{51}N_4O_8P$;
C=65.44, H=6.67, N=7.27;

Found C=65.35, H=6.73, N=7.29.

TABLE 1

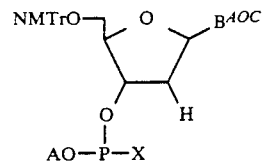

| Compound No. | Substituents | | |
|---|---|---|---|
| | A | X | $B^{AOC}$ |
| 4 | allyl | dimethylamino | thymine base |
| 5 | allyl | diisopropylamino | thymine base |
| 6 | allyl | morpholino | adenine base protected with allyloxycarbonyl |
| 7 | allyl | dimethylamino | guanine base protected with allyloxycarbonyl |
| 8 | allyl | diisopropylamino | cytosine base protected with allyloxycarbonyl |

REFERENCE EXAMPLE 6

Synthesis of a dimer 3.12 Millimoles of compound 4 obtained in Referential Example 4 was dissolved in 15 ml of a 1:2 mixed solvent of tetrahydrofuran and acetonitrile, and then 2.86 millimoles of 3'-o-t-butyldimethylsilyl-thymidine and 3.42 millimoles of 1-H-tetrazole were added. The mixture was stirred at 20° C. for 2 hours The reaction mixture was cooled to −78° C., and a dichloromethane solution of 4.86 millimoles of nitrogen dioxide was added. The oxidation was carried out for 30 minutes, and then the 30 ml of an aqueous solution of 0.5 mole of sodium sulfite was added. The temperature was returned to room temperarture, and chloroform and a saturated aqueous solution of sodium chloride were added. The aqueous layer was separated, extracted with chloroform, dried and then chromatographed on a silica gel column (silica gel 120 g; methanol:chloroform=1:-30–1:20) to give allyl-5')-o-monomethoxytritylthymidilyl-(3'43 5')-dimethylsilylthymide (compound 9) in a yield of 86%. The resulting substance had the following properties.

(1) $Rf(SiO_2$, methanol/ethyl acetate/hexane
=1:50:25)
0.38
(2) 1H NMR($CDCl_3$)
0.09(s, 6H, 2 $SiCH_3$), 0.89(s, 9H, $SiC(CH_3)_3$),
1.41, 1.90 (each s, 6H, 2 5—CH3), 2.1–2.8(m,
4H, $4H_2$'2), 3.44(m, 2H, 2 ), 3.79(s, 3H,
OCH ), 3.95–4.7(m, 7H, , $2H_4$ ', $2H_5$',
$CH_2CH$=), 5.1–5.5(m, 3H, $H_3$', =$CH_2$),
5.65–6.08(m, 1H, CH=$CH_2$), 6.1–6.4(m, 2H,
$2H_1$'), 6.8, 7.15–7.5(m, 14H, Ar-H),
7.67 (brs, 2H, 6-H), 9.48(brs, 2H, 2NH)
(3) IR($CHCl_3$) 3350, 2900, 1700, 1680, 1595, 1250 $cm^{-1}$
(4) UV($CH_3OH$)
$\lambda_{max}$=266 nm
(5) Analysis
Calculated for $C_{49}H_{61}N_4O_{13}PSi$:
C=60.47, H=6.33, N=5.75;
Found: C=60.65, H=6.08, N=5.71.
(6) 31P NMR($CDCl_3$: $C_6H_6$1:1)

REFERENTIAL EXAMPLE 7

Deprotection of the dimer

Compound 9 (0.084 millimole) and 0.0252 millimole of triphenylphosphine were dissolved in 1 ml of tetrahydrofuran in an argon atmosphere, and then 0.0042 millimole of tetrakis(triphenylphosphine) palladium (0) dissolved in 1 ml of tetrahydrofuran was added. The mixture was stirred at room temperature for 5 minutes. Then, 36 microliters of n-butylamine was added, and the mixture was stirred for 20 minutes. The solvent was evaporated, and the residue was chromatographed (ODS, water:methanol=1:4) to give the corresponding dinucleoside phosphate (compound 10) with elimination of the allyl group in a yield of 80 mole%.

(compound 9)

(compound 10)

MMTr = monomethoxytrityl group
TSB = t-butyldimethylsilyl group

Synthesis of a dimer

Referential Example 6 was repeated except that compound 6 was used instead of compound 4. There was obtained allyl-5'-o-monomethoxytrityldeoxyadenosilyl (3→5')-3'-o-t-butyldimethylsilylthymidine thymidine (compound 11) in a yield of 85%. This substance had the following properties.

(1) $^1H$ NMR(CDCl$_3$)

83(each s, 6H, Si(CH$_3$)hd 2, 0.88(s, 9H, SiC(CH$_3$)$_8$), 1.36(s, 3H, —CH$_3$), 2.23–2.90 (m, 4H(2')), 3.32–3.50(m, 2H), 3.77(s, 3H —OCH$_3$), 4.00–4.80(m, 8H), 5.03–5.54(m, 6H), 5.58–6.2

(m, 2H, ），

6.33–6.57(m, 2H(1')), 6.77(s, 1H, (Ar)), 6.87(s, 1H, (Ar)), 7.08–7.43(m, 12H, (Ar)), 7.48–7.57(b, 1H), 8.20, 8.24(each s, 1H), 8.73(s, 1H).

(2) Analysis

Calculated: C=59.70, H=6.06, N=9.20;
d C=59.85, H=6.01, N=9.14.

REFERENTIAL EXAMPLE 9

Deprotection on of the dimer

Compound 11 (0.103 millimole) was dissolved in ml of tetrahydrofuran, and 0.406 millimole of n-butylamine and 0.434 millimole of formic acid were successively added dropwise. Then, a solution of 0.0104 millimole of tetrakis(triphenylphosphine) palladium (0) in 1.5 ml of tetrahydrofuran was added, and the mixture was stirred at room temperature for 20 minutes.

After the reaction, the solvent was evaporated, and ethyl acetate and water were added to the residue to separate it into an organic layer and an aqueous layer. The organic layer was washed with a saturated aqueous solution of sodium chloride, dried over magnesium sulfate, and concentrated. The residue was chromatographed to give a dinucleoside phosphate (compound 12) in a yield of 90 mole% with elimination of the allyl group in the phosphorus moiety and the allyloxycarbonyl group in the base portion.

(compound 11)

(compound 12)

AOC = allyloxycarbonyl group

REFERENTIAL EXAMPLE 10

Synthesis of a dimer:

Compound 7 (3.12 millimoles) obtained in Example 2 was dissolved in 15 ml of a 1:2 mixed solvent of tetrahydrofuran and acetonitrile, and then 2.86 millimoles of 3'-o-t-butyldimethylsilyl-N-allyloxycarbonyl-2'deoxycytidine and 3.42 millimoles of 1-H-tetrazole were added. The mixture was stirred at 20° C. for 2 hours. The mixture was then cooled to −78° C., and a dichloromethane solution of 4.86 millimoles of nitrogen dioxide was added. The oxidation was carried out for 30 minutes, and then 30 ml of a 0.5 M aqueous solution of sodium sulfite was added. The temperature was returned to room temperature, and then chloroform and a saturated aqueous solution of sodium chloride were added. The separated aqueous layer was extracted with chloroform. After drying, the extract was chromatographed (silica gel 12 g; methanol:chloroform=1:30–1:20) to give allyl-5'-o-monomethyoxytrityl-N-allyloxycarbonyl-2'-deoxyguanosyl monomethoxytrityl-N-allyloxycarbonyl-2'-deoxyguanosyl (3'→5')-o-t-butyldimethylsilyl-N-allyloxycarbonyl-2'deoxycytidine (compound 13) in a yield of 86%. This substance had the following properties.

(1) Rf(SiO$_2$, methanol/ethyl acetate/hexane =1:50:25)
0.38

(2) $^1H$ NMR(CDCl$_3$) 0.09(s, 6H, 2SiCH$_3$), 0.89(s, 9H, SiC(CH$_3$)$_3$),
2.1–2.8(m, 4H$_2$', 4 ), 3.44(m, 2H, 2H'5),
3.79(s, 3H, 3.95–4.7(m, 11H, 2H'4,
3CH2CH=), 5.1–5.5(m 7H, H$_3$',
5.65–6.08(m, 3H, 3CH=CH ), 6.1–6.4
3=CH $_2$), 5.65–6.08(m, 3H, 3CH=CH$_2$), 6.1–6.4
(m, 2H, 2 , 6.8, 7.0–8.3(m, 17H Ar-H, 3H),
7.8–11.5(brs, 3H, NH, 2NHCO).

(3) Analysis

Calculated for C₅₆H₆₇N₈O₁₅PSi:
C=58.42, H=5.87, N=9.73;
Found: C=58.70, H=6.08, N=9.71.

REFERENTIAL EXAMPLE 11

Deprotection of the dimer:

Compound 13 (0.084 millimole) and 0.0252 milliCompound mole of triphenylphosphine were dissolved in 1 ml of tetrahydrofuran in an atmosphere of argon, and 0.0042 millimole of tetrakis(triphenylphosphine) palladium (0) was added. The mixture was stirred at room temperature for 5 minutes. Then, 36 microliters of n-butylamine was added. The mixture was stirred for 20 minutes, and the solvent was evaporated. The residue was chromatographed (ODS; water:methanol=1:4) to give the corresponding dinucleoside phosphate (compound 14) in a yield of 80 mole% with elimination of the allyl group and the allyloxycarbonyl group.

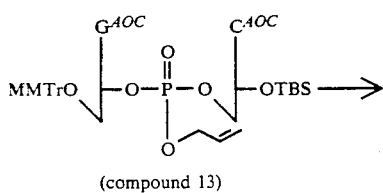

(compound 13)

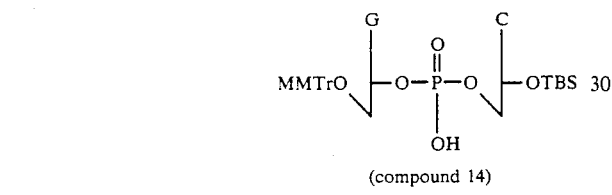

(compound 14)

MMTR = monomethoxytrityl group
TBS = t-butyldimethylsilyl group

REFERENTIAL EXAMPLE 12

Diisopropylamine (156 millimoles) was dissolved in 80 ml of diethyl ether, and then 34.7 millimoles of beta-cyanoethoxydichlorophosphine was added. The mixture was stirred at room temperature for 12 hours. After the reaction, the resulting diisopropyl ammonium chloride was separated by filtration. The ether solution was distilled to give beta-cyanoethoxymonochloro(N,N-diisopropylamino) phosphine as an oil. The yield was 73 mole%, and the product had a boiling point of 102 to 104° C. (0.08 mmHg).

The above beta-cyanoethoxydichlorophosphine was prepared by reacting one equivalent of phosphorus trichloride and one equivalent of beta-cyanoethanol in an organic solvent at −5° C. for 3 hours, distilling the reaction product under reduced pressure, and collecting distillates boiling at 110–112° C./9 mmHg.

EXAMPLE 4

1.5 Millimoles of 5'-o-dimethoxytrityl-N-allyloxydeoxycytidine (compound 15) obtained by reacting 5'-o-dimethoxytrityl-2'-deoxycytidine with allyl(1-benzotriazolyl)carbonate, and 1.56 millimoles of 1-H-tetrazole were dissolved in 12 ml of a 1:1 mixed solvent of tetrahydrofuran and acetonitrile, and then 2.25 millimoles of beta-cyanoethoxymonochloro(N,N-diisopropylamino)phosphine was added at 0° C. The mixture was stirred at 25° C. for 1.5 hours. The reaction mixture was diluted with ethyl acetate which had been washed with a saturated aqueous solution of sodium bicarbonate. The diluted mixture was washed with a saturated aqueous solution of sodium chloride, and the resulting organic layer was dried over magnesium sulfate and concentrated. The residue was dissolved in a 3:1 mixed solvent of toluene and hexane, and with vigorous stirring at −78° C., the solution was added to hexane to form a precipitate. The precipitate was separated by filtration. Its yield was 65%. Analysis of the precipitate led to the determination that it was a phosphoramidite (compound 16) of the following formula having the following properties.

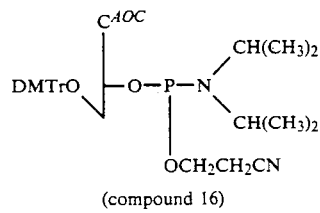

(compound 16)

AOC = allyloxycarbonyl group
DMTr = dimethoxytrityl group (1) Analysis
Calculated for C₄₃H₅₂O₉N₅P:
C=63.5, H=6.40, N=8.61;
Found: C=63.3, H=6.46, N=8.57.

(2) ¹H-NMR(CDCl₃)
4.04, 4.42(P—OCH₂), 3.81(N(CH)),
2.79(—CH₂CN), 1.30(—NC(CH₃)₂), 2.06–2.35
(1H(2'), 2.55(1H(2')), 3.30(1H(5')),
3.55(1H(5')), 3.84(6H(20CH₃)), 3.90–4.10
(1H(4')), 4.45(1H(3')), 4.46(2H(allyl)),

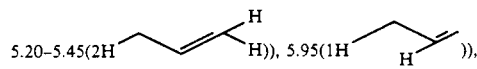

6.22(1H(1')), 6.50–7.45(14H(A), 8.37(1H).

EXAMPLE 5

0.2 Millimole of 5'-o-dimethoxytrityl-N-allyl-oxycarbonyl-2'-deoxyadenosine (compound 17) and 0.21 millimole of 1-H-tetrazole were dissolved in 2 ml of acetonitrile, and then 0.3 millimole of beta-cyanoethoxymonochloro(diisopropylamino)phosphine mixture was stirred at 25° C. for 1.5 hours. The reaction mixture was then worked up in the same way as in Example 4 to give a phosphoramidite (compound 18) of the following formula and properties in a yield of 62%.

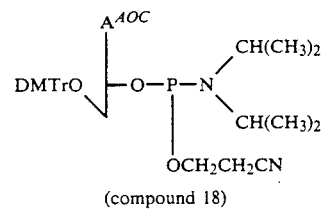

(compound 18)

(1) Analysis
Calculated for C₄₄H₅₅O₈N₇P;
C=63.1, H=6.21, N=11.7;
Found: C=63.0, H=6.29, N=11.0.

(2) ¹H—NMR(CDCl₃)
3.41(2H(5')), 3.7(3H(OCH₃)), 4.15(1H(4'),
4.76(2H(allyl)),

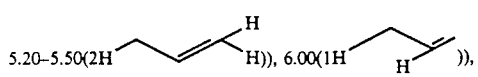

6.49(H(1')),,
6.55–7.41(14H(Ar)), 8.37(1H), 8.47(1H (amide)),
8.68(1H).

REFERENTIAL EXAMPLE 13

Synthesis of a dimer:

Compound 16 (3.12 millimoles) obtained in Example 4 was dissolved in 15 ml of a 1:2 mixed solvent of tetrahydrofuran and acetonitrile, and then 2.86 millimoles of 3'-o-t-butyldimethylsilylthymidine and 3.42 millimoles of 1-H-tetrazole were added. The mixture was stirred at 20° C. for 2 hours. The reaction mixture was cooled to −78° C. and then oxidized for 30 minutes by adding 4.86 millimoles of nitrogen dioxide as a dichloromethane solution. Then, 30 ml of a 0.5 M aqueous solution of sodium sulfite was added. Chloroform and a saturated aqueous solution of sodium chloride were added. The aqueous layer that separated was extracted with chloroform. The extract was dried, and then chromatographed (silica gel 120 g; methanol:chloroform = 1:30–1:20) to give beta-cyanoethyl-5'-o-dimethoxytrityl-cytidilyl-(3'5')-3'-o-t-butyldimethylsilylthymidine (compound 19) in a yield of 80%. The substance had the following properties.

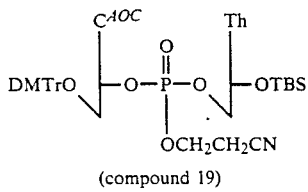

(compound 19)

TBS = t-butyldimethylsilyl group

Analysis
Calculated for $C_{53}H_{65}O_{15}N_6SiP$:
C = 58.67, H = 6.00, N = 7.75;
Found: C = 58.49, H = 6.02, N = 7.88.

REFERENTIAL EXAMPLE 14

Deprotecion of the dimer:

Compound 19 (0.084 millimole) and 0.0252 millimole of triphenylphosphine were dissolved in 1 ml of tetrahydrofuran in an atmosphere of argon, and 0.0042 millimole of tetrakis(triphenylphosphine)palladium (0) was added. The mixure was stirred at room temperature for 5 minutes. Then, 36 microliters of n-butylamine was added. The mixture was stirred for 20 minutes. The solvent was evaporated, and the residue was reacted with aqueous ammonia for 20 minutes at room temperature. Ammonia was then evaporated, adn the residue was chromatographed (ODS; water:methanol = 1:4) to give the corresponding dinucleoside phosphate (compound 20) in a yield of 77 mole% with elimination of the allyloxycarbonyl and the cyanoethyl group.

(compound 20)

Analysis
Calculated for $C_{46}H_{58}O_{13}N_5SiP$:
C = 58.29, H = 6.12, N = 7.39;
Found: C = 58.33, H = 6.06, N = 7.51.

REFERENTIAL EXAMPLE 15

Thirty milligrams of 5'-o-dimethoxytritylthymidine (compound 21) bonded to CPG (controlled pore glass) through an ester linkage was put in a glass reactor, and a dichloromethane solution of trichloroacetic acid was added to deprotect the 5'-hydroxyl group. The product was washed with acetonitrile. Then, a solution of 0.03 millimole of the phosporamidite (compound 16) in which the amino group of the cytidine base was protected with an allyloxycarbonyl group and 0.04 millimole of 1-H-tetrazole in a mixed solvent of acetonitrile and tetrahydrofuran was added, and reacted at room temperature for 2 minutes. The reaction mixture was washed with acetonitrile, and 1.2 ml of an iodine solution (composed 11.6 g of iodine, 18 ml of water, 180 ml of lutidine and 720 ml of tetrahydrofuran) was added. The reaction was carried out for 25 seconds to give a C-T dimer (compound 22) supported on a carrier. The yield was 80% (determined by color formation incident to the liberation of the 5'-dimethoxytrityl group.

The compound was identified by the following procedure.

The carrier containing the compound 22 was washed with acetonitrile and then acetic anhydride was added to cap the unreacted 5'-hydroxyl group. The product was washed with acetonitrile. Then, a solution of 0.095 millimole of triphenylphosphine, 0.6 millimole of n-butylamine, 0.6 millimole of formic acid and 0.015 millimole of tetrakis(tri phenylphosphine) palladium (0) in tetra hydrofuran was added, and the mixture was reacted at room temperature for 10 minutes to deprotect the allyloxycarbonyl group in the base moiety.

The product was washed with tetrahydrofuran and dichloromethane, and the dimethoxytrityl group at the 5'-hydroxyl group was eliminated by trichloroacetic acid to give a compound 23. Then, a 30% aqueous solution of ammonia was added, and the mixture left to stand at room temperature for 30 minutes to remove the carrier and the beta-cyanoethyl group in the phosphoric acid moiety to give a dimer of C-T (compound 24).

Ammonia was evaporated, and the residue was dissolved in 200 microliters of water. Then, 5 microliters of the aqueous solution was sampled. One microliter of [γ-$^{32}$P]ATP (PB-170, a product of Amersham Co.) was added, and the mixture was dried. The dried product was kinated (phosphorized) by adding 2 microliters of a kinase buffer (×2.5), 1 microliter of T$_4$ nucleotide kinase (2.5 U/microliter, a product of Takara Shuzo Co., Ltd.) and 2 microliters of water. The product was developed on TLC (Polygram, CELL300 KDEAE/HR-2/15, a product of MackereyNagel Co.,) with RNA homomixture to obtain a one dimensional autoradiograph which showed that there was a single spot. The position of one spot was extracted from TLC, and digested with venomphosphodiesterase and nuclease Pl. The digestion product was developed by electrophoresis using DEAE-cellulose paper, transferred to TLC, and two-dimensionally developed with a homomixture. After the two-dimensional development, the TLC was autoradiographed, and it was determined from the position of the spot that a CT dimer with elimination of the protective group was formed.

in which the amino or imino group is protected with an allyloxycarbonyl residue, with the proviso that only one of $R_1$, $R_2$ and $R_3$ represents the group —$OR_4$.

2. The compound of cliam 1 wherein $R_1$ is a hyrdoxyl group having a protective group, and $R_2$ is the group —$OR_4$.

3. The compound of claim 1 wherein $R_3$ is a hydrogen atom.

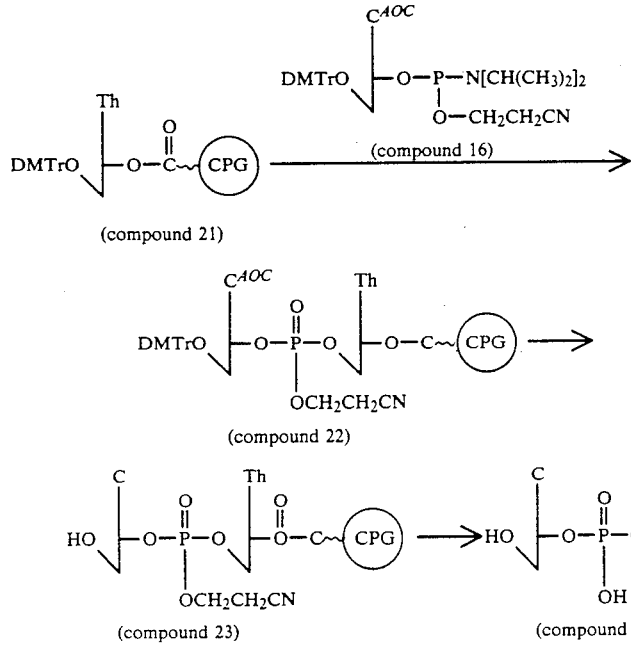

What is claimed is:

1. A phosphoramidite commpound of the general formula

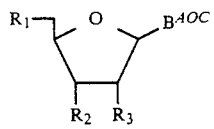

wherein each of $R_1$ and $R_2$, represents a hydroxyl group having an hydroxyl protective group or the group —$OR_4$, $R_3$ represents a hydrogen atom, a hydroxyl group having an hydroxyl protective group, or the group —$OR_4$ wherein the protective group for the hydroxyl group in $R_1$, $R_2$ and in $R_3$ when $R_3$ is a hydroxyl group having a protective group, is independently selected from the group consisting of trityl, monomethoxytrityl, dimethoxytrityl, trimethylsilyl, triethylsily, triphenylsilyl, t-butyldimetylsilyl, tetrahydropyranyl, 4-methoxyhydrofuranyl, benzoyl, tetrahydrofuranyl, methoxymethyl, methoxyethoxymethyl, phenoxymethyl, methylthiomethyl and phenylthiomethyl, $R_4$ represents the group

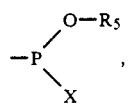

X represents a secondary amino group, $R_5$ represents an allylic residue having not more than 10 carbon atoms and which does not essentially impede the deprotecting reaction, and $B^{AOC}$ represents a nucleoside base residue 4. The compound of claim 1 wherein X is a secondary amino group having not more than 10 carbon atoms.

5. The compound of claim 1 wherein AOC is an allyloxycarbonyl residue having not more than 12 carbon atoms.

6. The compound of claim 1 wherein the nucleoside is adenosine, guanosine, cytidine or isosine.

7. A phosphoramidite compound of the general formula

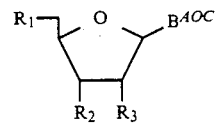

wherein each of $R_1$ and $R_2$, represents a hydroxyl group having an hydroxyl protective group, or the group —$OR_4$, $R_3$ represents a hydrogen atom, a hydroxyl group having an hydroxyl protective group, or the group —$OR_4$ wherein the protective group for the hydroxyl group in $R_1$, $R_2$ and in $R_3$ when $R_3$ is a hydroxyl group having a protective group, is independently selected from the group consisting of trityl, monomethoxytrityl, dimethoxytrityl, trimethylsily, triethylsilyl, triphenylsilyl, t-butyldimethylsilyl, tetrahydropyranyl, 4-methoxyhydrofuranyl, benzoyl, benzyl, tetrahydrofuranyl, methoxymethyl, methoxyethoxymethyl, phenoxymethyl, methylthiomethyl and phenylthiomethyl, $R_4$ represents the group,

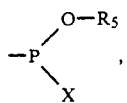

X represetns a secondary amino group, R$_5$ is a group represented by the general formula

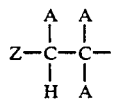

wherein A represents a hydrogen atom or a lower alkyl group selected from the group consisting of ethyl and methyl groups, and Z represents an electron attracting residue selected from the group consisting of a cyano group, nitro group, thiocyano group, fluoro group, chloro group, bromo group, phenylsulfonyl group, methylsulfonyl group and a phenyl group, wherein the phenyl group may have a substituent at its ortho and/or para position selected from the group consisting of halogen, cyano and nitro groups and B$^{AOC}$ represents a nucleoside base residue in which the amino or imino group is protected with an allylaoxycarbonyl residue, with the proviso tHat only one of R$_1$, R$_2$ and R$_3$ represents the group —OR$_4$.

8. The compound of claim 7 wherein R$_1$ is a hydroxyl group having a protective group and R$^2$ is the group —OR$^4$.

9. The compound of claim 7 wherein R$^3$ is a hydrogen atom.

10. The compound of claim 7 wherein X is a secondary amino group having not more than 10 carbon atoms.

11. The compound of claim 7 wherein Z is a cyano group.

12. The compound of claim 7 wherein AOC is an allyloxycarbonyl residue having not more than 12 carbon atoms.

13. The compound of claim 7 wherein the nucleoside is adenosine, guanosine, cytidine or inosine.

14. The compound of claim 1 wherein the allylic residue is selectd from the group consisting of allyl, methallyl, crotyl, phenyl, geranyl, cinnamyl and p-chlorocinnamyl.

* * * * *